(12) United States Patent
Essiger

(10) Patent No.: US 6,616,672 B1
(45) Date of Patent: Sep. 9, 2003

(54) SURGICAL INSTRUMENT FOR DISPLACING BONE PARTS

(76) Inventor: Holger K. Essiger, Speckweg 3, D-30900, Wedemark (DE)

(*) Notice: Subject to any disclaimer, the term of this patent is extended or adjusted under 35 U.S.C. 154(b) by 0 days.

(21) Appl. No.: 09/624,573

(22) Filed: Jul. 24, 2000

(30) Foreign Application Priority Data

Jul. 24, 1999 (DE) .......................... 199 34 889

(51) Int. Cl.⁷ .............................. A61F 2/38; A61C 3/00
(52) U.S. Cl. ........................................ 606/105; 433/7
(58) Field of Search .......................... 606/105, 90, 58, 606/57, 86; 433/7; 70/82, 83, 345, 346

(56) References Cited

U.S. PATENT DOCUMENTS

| | | | | |
|---|---|---|---|---|
| 1,436,925 A | * | 11/1922 | Wege et al. .............. 70/82 |
| 1,966,272 A | * | 7/1934 | Vance et al. .............. 70/82 |
| 3,866,607 A | * | 2/1975 | Forsythe et al. ........... 606/105 |
| 5,725,526 A | * | 3/1998 | Allard et al. ............. 606/105 |
| 5,904,479 A | * | 5/1999 | Staples .................. 433/7 |
| 6,171,313 B1 | * | 1/2001 | Razdolsky et al. ......... 606/86 |

* cited by examiner

*Primary Examiner*—Todd E. Manahan
(74) *Attorney, Agent, or Firm*—R W Becker & Associates; R W Becker

(57) ABSTRACT

A surgical instrument having at least one displacement element is provided for displacing bone parts. The apparatus includes an implantable, flat housing in which an adjusting device for the displacement element(s), embodied as bolts, is arranged. The adjusting device can be operated from outside the housing.

16 Claims, 1 Drawing Sheet

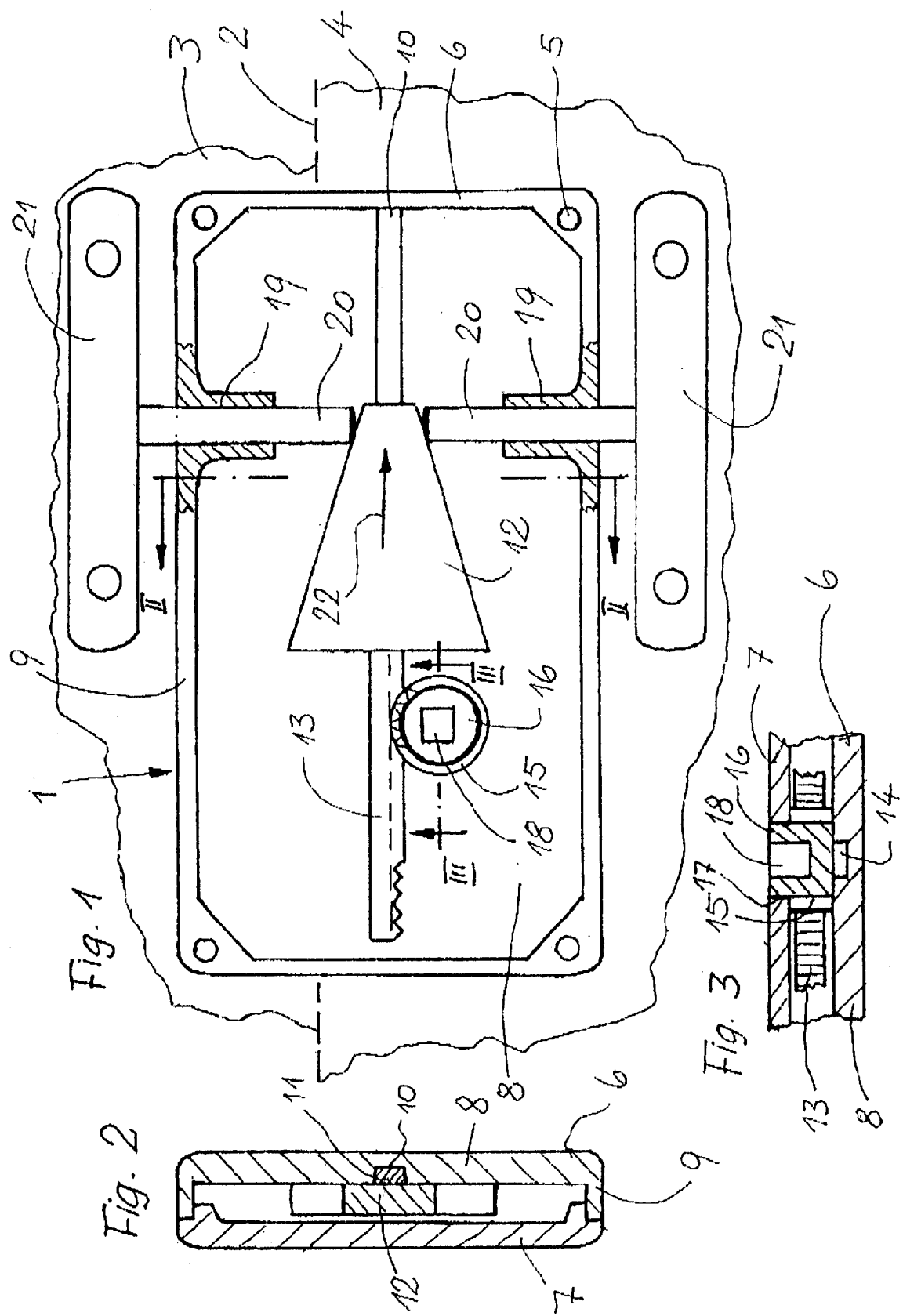

SURGICAL INSTRUMENT FOR DISPLACING BONE PARTS

BACKGROUND OF THE INVENTION

The present invention relates to a surgical instrument for displacing bone parts, preferably however an instrument for the expansion of hardened parts.

In particular, the invention is intended for use in surgery on the jaw, to be employed in cases of atrophy, impacted teeth or shrinkage where it is necessary for the purpose of regeneration to separate bone parts and to raise them relative to adjacent bones or to enlarge the distance between the bone part and the bone.

In the known instruments of this type, the bone part is displaced by helical displacement, whereby however elements of the instrument project into the oral cavity of the patient to such a degree that the use of the known instruments is very disturbing to the patient and there is a risk of infection in the mucous membranes and skin exit locations.

The object of the invention is to avoid these disadvantages by an inventive construction of the apparatus.

SUMMARY OF THE INVENTION

This object is inventively achieved in accordance with the invention in that an implantable, flat housing is provided in which is located an adjusting device for at least one displacement element, or for two displacement elements that are mutually opposably movable, that can be operated from the exterior via an opening in the housing; the displacement element or elements are longitudinally displaceable bolts that act on counterbearings that are detachably attached to the bones. The bolts are expediently moved by a cone that travels longitudinally with the travel thereof being effected by a toothed wheel or toothed member that can be operated from the exterior and that meshes with a toothed rod attached to the cone.

The housing is preferably attached, for example by being screwed, to the bone or to the bone part to be displaced or raised. However, it is preferable to attach the housing to the actual bone rather than only to a part of the bone.

It is important that the displacement device be encapsulated in a housing that is implantable due to the flat shape of the housing. This arrangement of the instrument beneath the soft tissue ensures that the patient's discomfort is kept to a minimum. The instrument, in accordance with the invention, is thus patient-friendly and can be used on patients who previously could not tolerate or endure such a surgical procedure.

BRIEF DESCRIPTION OF THE DRAWINGS

Additional details of the invention are explained with reference to the drawing, in which is illustrated an exemplary embodiment of the invention.

FIG. 1 is a plan view of an apparatus for the expansion of hardened parts in the region of the human jaw in the form of a flat housing with the cover removed, and enlarged in scale;

FIG. 2 is a cross-section taken along the line II—II in FIG. 1; and,

FIG. 3 is a cross-section taken along the line III—III in FIG. 1.

DESCRIPTION OF PREFERRED EMBODIMENTS

An essential component of the instrument in accordance with the invention is a housing 1 that has a flat and rectangular contour and that is made of a material suitable for implantation, e.g. titanium. Preferably the dimensions thereof are about 3.5–5 cm×1.5–2.5 cm, with a thickness of about 1.5–3 mm; however, these dimensions can be altered if necessary for particular applications. This housing 1 should lie beneath the soft tissue directly on the bone.

The bone separation line, provided e.g. by a saw, is labeled 2. The part of the bone to be lifted is labeled 3 and the actual bone is labeled 4. In the present case the housing 1 should lie on the bone 4. Provided for attaching the housing 1 are holes 5 with which the housing 1 can be screwed on.

The housing 1 comprises a lower part 6 and a cover 7, whereby these parts engage in an exact fit. Although not shown, conventional locking elements can also be provided. The base of the lower part 6 is labeled 8 and the circumferential lateral walls of the lower part 6 are labeled 9.

Provided in the base 8 and running lengthwise relative to the housing 1 is a central groove 10 into which engages a rib 11 of a symmetrical cone 12, which in the extension of its longitudinal center axis has a rearwardly extending toothed rod 13 that meshes with a toothed wheel 15 borne on the base 8 by means of a pin 14. This toothed wheel extends upward via a hub 16 that is borne in a round recess 17 in the cover 7. The hub 16 also has at its free end a square keyhole 18, which naturally can also be replaced by the frequently-used hexagonal keyhole.

Thus, when the housing 1 is closed, this square hole 18 is accessible from the outside. A suitable key can be inserted therein in order to turn the toothed wheel 15, thereby moving the cone 12.

Provided on both sides of the cone 12 in the lateral walls 9 are supports or bearings 19 for longitudinally displaceable bolts 20 that act upon abutments or counterbearings 21 that are outside the housing and that are securely screwed to the bone 3, 4.

The ends of the bolts 20 which are located inside the housing 1 abut the lateral inclined surfaces of the cone 12. Consequently, when the cone moves in the direction of the arrow 22, the bolts 20 are outwardly displaced and thus the bone 3 is lifted or raised.

In order to avoid moving the cone 12 in opposition to the direction of the arrow 22, reverse travel stops of any type can be provided that also must be releasable from the outside. However, these stops are not mandatory and it is possible to do without them if the cone incline itself inhibits reverse travel.

The bolts 20 can be either loose elements or components of the counterbearings 21. However, it is important that when two bolts 20 are used there is an opposing movement for displacing the bone or parts thereof.

The adjusting device for the opposing bolts 20 is consequently hermetically sealed in the housing 1. In addition, the adjusting device can also be actuated from the outside by simply turning the toothed wheel 15.

It is furthermore important that the housing 1 is kept very flat. Therefore the movable elements 12, 13, 15 located therein are secured against undesired misalignment. The interior surfaces of the housing 1 constitute a stop for these elements. In addition, the bearings 19 provide secure bearing and guidance for the bolts 20.

Instead of the symmetrical cone as illustrated in the drawing, it is also possible to use an asymmetrical cone (with different inclines). Furthermore, if the housing 1 is anchored or held appropriately, it is possible to provide only one effective adjusting element or one bolt 20. Consequently, with reference to the drawing, one bolt 20 can be effective or can be omitted altogether. In this case a cone 12 that works only on one side would be sufficient. Finally, attaching the housing can be superfluous if the counterbearings 21 are anchored.

The specification incorporates by reference the disclosure of German priority document 199 34 889.8 of Jul. 24, 1999.

The present invention is, of course, in no way restricted to the specific disclosure of the specification and drawings, but also encompasses any modifications within the scope of the appended claims.

What I claim is:

1. A surgical instrument for displacing bone parts, comprising:
    a flat, implantable housing having an opening;
    at least one longitudinally movable displacement element in the form of a bolt guided by said housing; and
    an adjusting device disposed in said housing for actuating said at least one displacement element, wherein said adjusting device is operable from outside said housing via said opening of said housing, wherein said adjusting device includes a displaceable cone having at least one inclined surface for acting upon said at least one displacement element, and wherein said cone includes a toothed rod that meshes with a toothed wheel of said adjusting device, wherein said toothed wheel is rotatable from outside said housing.

2. A surgical instrument according to claim 1, wherein said at least one displacement element comprises two bolts that are movable in opposite directions.

3. A surgical instrument according to claim 1, which includes bearing means disposed in side walls of said housing for said at least one displacement element.

4. A surgical instrument according to claim 1, wherein said toothed wheel includes a hub-like extension for tightly engaging said opening of said housing, wherein said extension is embodied for receiving a tool for operating said toothed wheel.

5. A surgical instrument according to claim 4, wherein said extension is provided with a recessed portion for receiving said tool.

6. A surgical instrument according to claim 1, wherein said housing has a flat configuration such that it has a confined interior space provided by inner housing surfaces that prevent movable components of said adjusting device from leaving an operative position within said housing.

7. A surgical instrument according to claim 1, wherein said housing is provided with holes to receive screws for securing said housing to bones.

8. A surgical instrument according to claim 1, wherein said at least one displacement element cooperates with counterbearing means that are secured to bones.

9. A surgical instrument according to claim 1, wherein longer ones of side edges of said housing extend parallel to a longitudinal central axis of said cone.

10. A surgical instrument according to claim 1, wherein said housing is provided with a removable cover.

11. A surgical instrument according to claim 1, wherein said housing has a width of approximately 1.5–2.5 cm, a length of approximately 3.5–5 cm, and a thickness of approximately 1.5–3 mm.

12. A surgical instrument for displacing bone parts, comprising:
    a flat, implantable housing having an opening;
    at least one longitudinally movable displacement element in the form of a bolt guided by said housing; and
    an adjusting device disposed in said housing for actuating said at least one displacement element, wherein said adjusting device is operable from outside said housing via said opening of said housing, wherein said adjusting device includes a displaceable cone having at least one inclined surface for acting upon said at least one displacement element, and wherein said cone is provided with a projecting rib that is guided in a groove of said housing.

13. A surgical instrument according to claim 12, wherein said groove is provided in a base of said housing.

14. A surgical instrument for displacing bone parts, comprising:
    a flat, implantable housing having an opening;
    at least one longitudinally movable displacement element in the form of a bolt guided by said housing; and
    an adjusting device disposed in said housing for actuating said at least one displacement element, wherein said adjusting device is operable from outside said housing via said opening of said housing, wherein said bolt is displaceable in a displacement direction and said adjusting device includes a movement translation component movable within said housing along a driver direction generally perpendicular to said displacement direction along which said bolt is displaceable, said movement translation component and said bolt cooperating with one another such that movement of said movement translation component along said driver direction effects movement of said bolt along said displacement direction, and said housing has a flat configuration such that it has a confined interior space provided by inner housing surfaces that prevent movable components of said adjusting device from leaving an operative position within said housing, wherein said movement translating component of said adjusting device includes a displaceable cone having at least one inclined surface for acting upon said at least one displacement element, and wherein said at least one displacement element comprises two bolts that are movable in opposite directions and said displaceable cone includes another inclined surface, said at least one inclined surface of said displaceable cone cooperatively engaging a respective one of said bolts to displace said respective one bolt outwardly of said housing in response to actuation of said adjusting device and said another inclined surface of said displaceable cone cooperatively engaging the other of said bolts to displace said other bolt outwardly of said housing in a direction opposite to the displacing movement of said respective one bolt in response to actuation of said adjusting device.

15. A method of displacing bone parts of a patient, comprising:
    providing a surgical instrument, the surgical instrument having a flat, implantable housing, at least one longitudinally movable displacement element in the form of a bolt guided by said housing, and an adjusting device disposed in said housing for actuating said at least one displacement element;
    implanting the said housing in a patient below the patient's skin such that said at least one longitudinally movable displacement element engages a bone part to be displaced via longitudinal displacement of said at least one longitudinally movable displacement element; and
    actuating said adjusting device to thereby effect longitudinal displacement of said at least one longitudinally movable displacement element and consequent displacement of the respective bone part engaged thereby.

16. A method according to claim 15, wherein providing a surgical instrument includes providing said adjusting device with a movement translation component movable within said housing along a driver direction generally perpendicular to a displacement direction along which said bolt is displaceable and actuating said adjusting device includes moving said movement translation component along said driver direction into engagement with said bolt in a manner in which said movement translation component and said bolt cooperate with one another such said movement translation component effects movement of said bolt along said displacement direction.

\* \* \* \* \*